United States Patent
Oliveira et al.

(10) Patent No.: US 11,295,867 B2
(45) Date of Patent: *Apr. 5, 2022

(54) GENERATING AND APPLYING SUBJECT EVENT TIMELINES

(71) Applicant: KONINKLIJKE PHILIPS N.V., Eindhoven (NL)

(72) Inventors: Lucas De Melo Oliveira, Wilmington, MA (US); Gabriel Ryan Mankovich, Boston, MA (US); Qianxi Li, Cambridge, MA (US)

(73) Assignee: Koninklljke Philips N.V., Eindhoven (NL)

( * ) Notice: Subject to any disclaimer, the term of this patent is extended or adjusted under 35 U.S.C. 154(b) by 149 days.

This patent is subject to a terminal disclaimer.

(21) Appl. No.: 16/430,718

(22) Filed: Jun. 4, 2019

(65) Prior Publication Data

US 2019/0371475 A1     Dec. 5, 2019

Related U.S. Application Data

(60) Provisional application No. 62/680,692, filed on Jun. 5, 2018.

(51) Int. Cl.
*G16H 50/70* (2018.01)
*G06N 20/00* (2019.01)
(Continued)

(52) U.S. Cl.
CPC .............. *G16H 50/70* (2018.01); *G06N 5/003* (2013.01); *G06N 20/00* (2019.01); *G16H 10/60* (2018.01)

(58) Field of Classification Search
CPC ... G06F 1/00–2221/2153; G16H 10/00–80/00; G06N 3/00–99/007
See application file for complete search history.

(56) References Cited

U.S. PATENT DOCUMENTS

| | | | |
|---|---|---|---|
| 7,444,293 B1* | 10/2008 | Kahn | G16H 70/20 |
| | | | 705/3 |
| 2006/0052945 A1* | 3/2006 | Rabinowitz | G16B 40/00 |
| | | | 702/20 |

(Continued)

FOREIGN PATENT DOCUMENTS

JP     2009518732 A * 5/2009 ............. G16H 10/60

OTHER PUBLICATIONS

Dabek et al., "A Timeline-based Framework for Aggregating and Summarizing Electronic Health Records," 2017 IEEE Workshop on Visual Analytics in Healthcare Oct. 1, 2017, Phoenix, Arizona. (Year: 2017).*

(Continued)

*Primary Examiner* — Elaine Gort
*Assistant Examiner* — Jonathon A. Szumny

(57) ABSTRACT

Techniques disclosed herein relate to generating and applying subject event timelines for various purposes. In various embodiments, data indicative of medical events associated with a subject may be retrieved from various data sources. Each of the medical events may be associated with a respective timestamp. Based on the medical events and associated timestamps, a timeline data structure associated with the subject may be assembled. The timeline data structure may be analyzed to identify inconsistenc(ies) between medical events associated with the subject. A visual timeline indicative of the medical events may be rendered on a display based on the timeline data structure. Each respective medical event may be represented in the visual timeline by a graphical element. Two or more of the graphical elements that are associated with the medical events for which the inconsistenc(ies) were identified may be visually distinguished.

11 Claims, 11 Drawing Sheets

(51) Int. Cl.
*G06N 5/00* (2006.01)
*G16H 10/60* (2018.01)

(56) References Cited

U.S. PATENT DOCUMENTS

| | | | |
|---|---|---|---|
| 2007/0094188 A1* | 4/2007 | Pandya | G16H 50/20 |
| | | | 706/45 |
| 2007/0100821 A1* | 5/2007 | Freeman | G06F 16/951 |
| 2007/0100822 A1* | 5/2007 | Freeman | G06F 16/90335 |
| 2008/0077887 A1* | 3/2008 | Malnati | G06F 16/2477 |
| | | | 715/855 |
| 2008/0201280 A1* | 8/2008 | Martin | G06N 20/00 |
| | | | 706/12 |
| 2010/0256991 A1* | 10/2010 | Ishikawa | G16H 50/20 |
| | | | 705/3 |
| 2013/0290008 A1* | 10/2013 | Rosenblum | G16H 10/20 |
| | | | 705/2 |
| 2014/0257047 A1* | 9/2014 | Sillay | A61B 5/4082 |
| | | | 600/301 |
| 2014/0278448 A1* | 9/2014 | Sadeghi | G16H 15/00 |
| | | | 705/2 |
| 2014/0350961 A1* | 11/2014 | Csurka | G16H 10/60 |
| | | | 705/3 |
| 2015/0088888 A1* | 3/2015 | Brennan | G06F 16/38 |
| | | | 707/737 |
| 2015/0254598 A1* | 9/2015 | Engels | G06Q 10/063114 |
| | | | 705/2 |
| 2016/0267442 A1* | 9/2016 | Richardson | G06Q 10/1095 |
| 2017/0286626 A1* | 10/2017 | Jayaku | G16H 15/00 |
| 2018/0095938 A1* | 4/2018 | Monte | G06F 3/0488 |
| 2018/0301222 A1* | 10/2018 | Dew, Sr. | G06N 5/022 |
| 2018/0374057 A1* | 12/2018 | Vardidze | G06F 3/0485 |
| 2019/0244121 A1* | 8/2019 | Li | G06N 5/046 |
| 2019/0286743 A1* | 9/2019 | Lecue | G16H 70/40 |
| 2019/0332630 A1* | 10/2019 | Tonkin | G06F 16/86 |

OTHER PUBLICATIONS

Wang et al., "Aligning Temporal Data by Sentinel Events: Discovering Patterns in Electronic Health Records," CHI 2008 Proceedings Health and Wellness Apr. 5-10, 2008 • Florence, Italy. (Year: 2008).*

Hirsch et al., "HARVEST, a longitudinal patient record summarizer," J Am Med Inform Assoc 2015; 22:263-274. (Year: 2015).*

Gill et al., "Presenting patient data in the electronic care record: the role of timelines," J R Soc Med Sh Rep 2010;1:29. (Year: 2010).*

Bui et al., "TimeLine: Visualizing Integrated Patient Records," IEEE Transactions on Information Technology in Biomedicine, vol. 11, No. 4, Jul. 2007. (Year: 2007).*

* cited by examiner

GENERATING AND APPLYING SUBJECT EVENT TIMELINES

CROSS-REFERENCE TO RELATED APPLICATION

The present application claims priority to and the benefit of U.S. Provisional Application Ser. No. 62/680,692, filed Jun. 5, 2018, which is hereby incorporated by reference herein.

TECHNICAL FIELD

Various embodiments described herein are directed generally to health care. More particularly, but not exclusively, various methods and apparatus disclosed herein relate to generating and applying subject event timelines for various purposes.

BACKGROUND

As populations of patients (or more generally, "subjects") grow it becomes increasingly important to be able to generate succinct and uniform information about the subjects for a variety of purposes, such as reliably comparing subjects, identifying similar subjects (i.e. a "subject cohort"), detecting patterns amongst subjects, identify subject risks, and so forth. This may be particularly advantageous in scenarios such as clinical trials, insurance investigations/research, and/or in building analytics tools for whole institutions or clinical networks. Moreover, to assess a patient problem or make an intervention decision, clinicians often must combine and correlate large amounts of information, such as the patient's status, symptoms and treatments, stored in the patient health record over time. The adoption of healthcare informatics systems such as Electronic Medical Record ("EMR"), Radiology Information System ("RIS") and Laboratory Information System ("LIS") allowed medical personal to have access to an enormous amount of patient data. Unfortunately, these data are spread across different healthcare silos and under different management, leading to data heterogeneity. Consequently, it is currently difficult to compare subjects, identify similar subjects, and/or detect patterns amongst subjects without performing significant manual data manipulation. This leads to substantial costs, increased time to market for clinical drugs, and/or longer cycle times for analytics results. In addition, considerable human and computing resources may be required for this manual analysis.

SUMMARY

The present disclosure is directed to methods and apparatus for generating and applying subject event timelines for various purposes. For example, in various embodiments, a plurality of "medical events" and/or "medical concepts" associated with a subject may be extracted from a plurality of disparate data sources. The medical events may include, for instance, diagnoses, lab results, observed and/or reported symptoms, applied treatments, drug prescriptions, subject activities, insurance claims, etc.

The disparate data sources from which the medical events are extracted may include, for instance, structured data sources that include structured, non-narrative data records that convey information indicative of medical events. For example, hospital information systems ("HIS"), electronic medical records ("EMR"), laboratory information systems ("LIS"), and other data sources may include lab results, vital sign measurements, and other quantitative data points, and/or medical codes that are "structured," i.e., they are quantitative in nature and easily extracted. The disparate data sources may also include narrative data sources that include, for instance, narrative data records that describe medical events using free-formed prose. For example, clinical notes composed by a clinician may not necessarily be structured, and different clinicians may document the same medical event using different prose, even though both are trying to convey the same semantic meaning. In various embodiments, techniques such as natural language processing, topic classification, etc., may be employed to extract concepts associated with medical events from narrative data records.

In various embodiments, timestamps associated with the extracted medical events may also be determined. In most cases the timestamps may be obtained from the underlying data source, e.g., in the form of metadata, database record field, etc. Once the medical events and associated timestamps for a given subject are determined, they may be used to generate/assemble what will be referred to herein as a "timeline data structure" that represents a temporally ordered sequence of medical events associated with the given subject. The timeline data structure may be generated in various formats, such as a linked list, an array of medical events and associated timestamps, a sequence of database records, etc. Once the timeline data structures are assembled, they may be stored in one or more databases so that they can be used for various purposes.

In some embodiments, each timeline data structure may be used to render, e.g., as part of a graphical user interface ("GUI"), a visual timeline that includes graphical elements representing medical events associated with the respective subject. Due to the temporal ordering and/or timestamps, the graphical elements are rendered in a temporal order in which they occurred, so that a user such as a clinician, insurance investigator, researcher, etc., is able to view the subject's clinical trajectory over time in an intuitive manner. Additionally, in some embodiments, each graphical element may be operable to cause additional information about the respective medical event to be output. Suppose a particular graphical element represents diagnosis of left ventricular hypertrophy ("LVH"). When the user clicks on the particular graphical element, a new interface (e.g., a pop-up window) may be rendered that displays at least part of the underlying record that lead to this diagnosis. For example, all or a portion of an electrocardiogram ("ECG") may be rendered so that the user can take a closer look.

Additionally or alternatively, in some embodiments, the graphical elements of a visual timeline may be operable for other purposes. For example, in some embodiments, one or more graphical elements of a visual timeline may be operable (e.g., selectable) to formulate a search query that is usable to find similar subjects. For example, a user may select two or more medical events of a visual timeline, e.g., by clicking on them. Because the elements are already ordered temporally, the user has, by definition, also selected an inherent temporal relationship between the two or more selected medical events. In some embodiments, the user may be able to specify one or constraints on the search, such a demographic constraints, temporal constraints, and so forth. For example, a user may specify, for two selected events, a maximum or minimum time interval that must occur between them in order to satisfy the search query.

Next, one or more responsive timeline data structures associated with one or more other subjects may be retrieved from a database based on the search query and any associated constraints. In some embodiments, additional visual timelines may be rendered on the display that are based on the retrieved one or more responsive timeline structures. In this manner, a user is able to view similar subjects, e.g., a patient cohort, that is defined based on the user's query. In various implementations, these other visual timelines may also be operable, e.g., to see the underlying data records associated with medical events of the other subjects.

In another aspect, timeline data structures associated with subjects may be analyzed to identify inconsistencies and/or conflicts between medical events/concepts. For example, a subject's diagnosis of type II diabetes might raise a conflict if found within a short time of another diagnosis for hypoglycemia. A variety of different approaches may be applied, alone and/or in combination, to identify inconsistencies/conflicts, including but not limited to rules-based approaches (e.g., heuristics), machine learning models, etc. Identified inconsistencies/conflicts may be displayed to a variety of different types of users (e.g., clinicians, insurance adjusters, researchers, patients, etc.) for a variety of different purposes. These purposes include but are not limited to clinical decision support ("CDS"), analysis of care provided across a health care entity/system, for insurance claim investigation, etc.

Generally, in one aspect, a method may include: retrieving, from a plurality of data sources, data indicative of a plurality of medical events associated with a subject; associating each of the plurality of medical events with a respective timestamp; assembling, based on the plurality of medical events and associated timestamps, a timeline data structure associated with the subject; analyzing the timeline data structure to identify one or more inconsistencies between two or more medical events of the plurality of medical events associated with the subject; and causing a visual timeline indicative of the plurality of medical events to be rendered on a display based on the timeline data structure, wherein each respective medical event of the plurality of medical events is represented in the visual timeline by a graphical element, and wherein two or more of the graphical elements that are associated with the two or more medical events for which the one or more inconsistencies were identified are visually distinguished from other graphical elements.

In various embodiments, the analyzing may include semantically analyzing the plurality of medical events, and the one or more inconsistencies include one or more semantic inconsistencies. In various embodiments, the semantic analyzing may include searching for identity relationships between two or more of the plurality of medical events. In various embodiments, the analyzing may include applying attributes of at least two of the plurality of medical events as input across a trained machine learning model to generate output, wherein the output is indicative of the one or more inconsistencies.

In various embodiments, the method may further include classifying each of the plurality of medical events into one of a predetermined number of temporal categories. In various embodiments, the analyzing includes refraining from comparing two medical events of the plurality of medical events that are classified into incompatible temporal categories. In various embodiments, the analyzing may include navigating a phenotype decision tree based on attributes of at least two of the plurality of medical events.

In addition, some implementations include one or more processors of one or more computing devices, where the one or more processors are operably coupled with memory and are configured to execute instructions stored the memory, and where the instructions are configured to cause performance of any of the aforementioned methods. Some implementations also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

As populations of patients (or more generally, "subjects") grow it becomes increasingly important to be able to generate succinct and uniform information about the subjects for a variety of purposes, such as reliably comparing subjects, identifying similar subjects (i.e. a "subject cohort"), detecting patterns amongst subjects, identifying subject risk (s), and so forth. Moreover, to assess a patient problem or make an intervention decision, clinicians often must combine and correlate large amounts of information, such as the patient's status, symptoms, and treatments, stored in the patient health record over time. While the adoption of various healthcare informatics systems allowed clinicians and others to have access to an enormous amount of subject data, these data are spread across different healthcare silos and under different management, leading to data heterogeneity. Consequently, it is currently difficult to compare subjects, identify similar subjects, and/or detect pattern amongst subjects without performing significant manual data manipulation. This leads to substantial costs, increased time to market for clinical drugs, and/or longer cycle times for analytics results. In addition, considerable human and computing resources may be required for this manual analysis. In view of the foregoing, various embodiments and implementations of the present disclosure are directed to generating and applying subject event timelines of medical events for various purposes.

Figure 1:
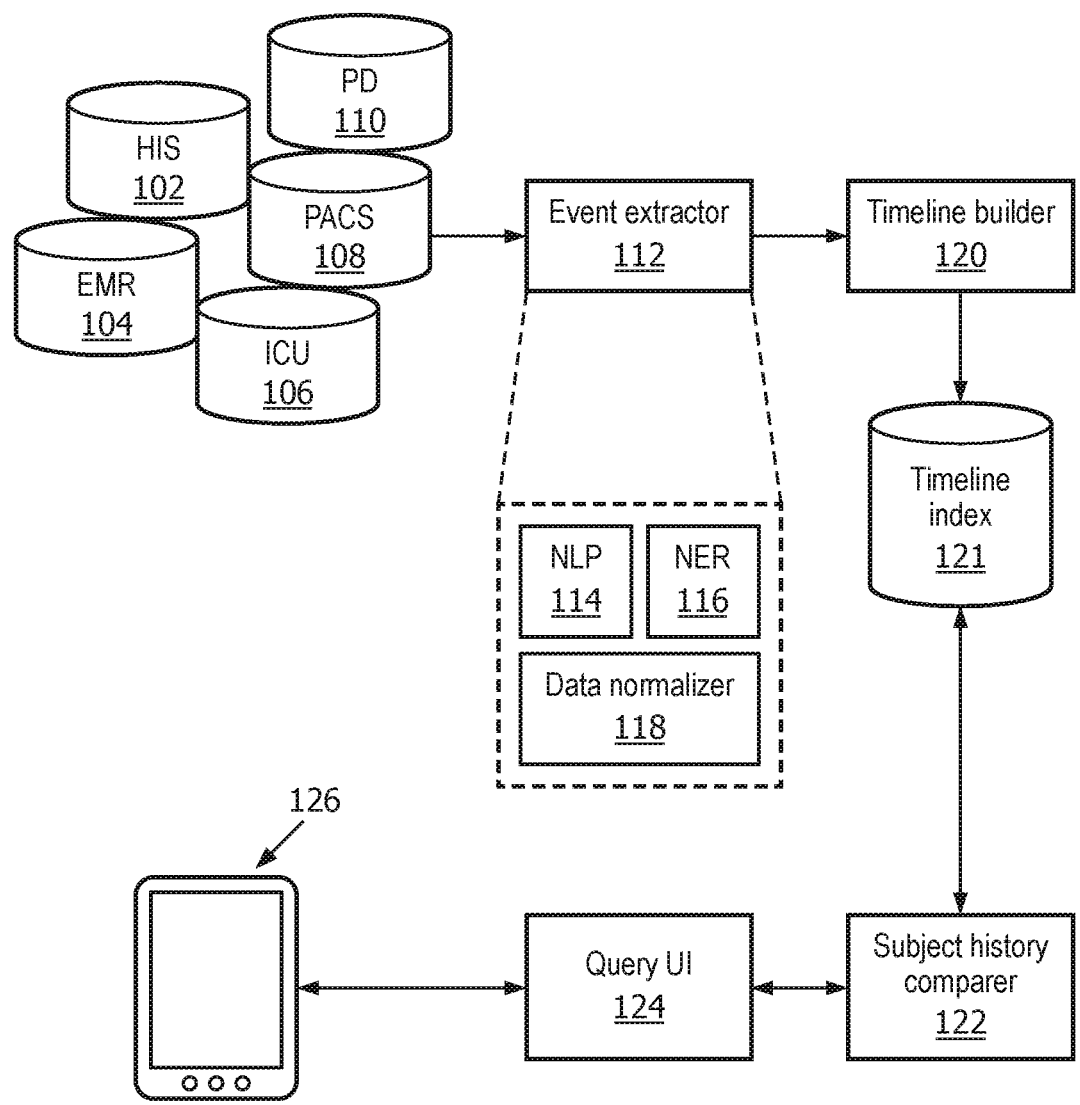
FIG. 1 illustrates an example environment in which selected aspects of the present disclosure may be implemented, in accordance with various embodiments.

Referring to FIG. 1, an example environment is depicted schematically, showing various components that may be configured to perform selected aspects of the present disclosure. One or more of these components may be implemented using any combination of hardware or software. For example, one or more components may be implemented using one or more microprocessors that execute instructions stored in memory, a field-programmable gate array ("FPGA"), and/or an application-specific integrated circuit ("ASIC"). The connections between the various components represent communication channels that may be implemented using a variety of different networking technologies, such as Wi-Fi, Ethernet, Bluetooth, USB, serial, etc. In embodiments in which the depicted components are implemented as software executed by processor(s), the various components may be implemented across one or more computing systems that may be in communication over one or more networks (not depicted).

As noted previously, medical data associated with subjects such as patients, insureds, etc., may be stored in a variety of disparate data sources. Each data source may store different types of data in different formats. In FIG. 1, a variety of health-related databases are depicted, including a hospital information system ("HIS") database 102, an electronic medical record ("EMR") database 104, an intensive care unit ("ICU") database 106, and a picture archiving and communication system ("PACS") database 108. One or more additional databases may be provided, and/or one or more of the databases depicted in FIG. 1 may be omitted and/or combined with one or more other databases depicted in FIG. 1. Also depicted as a database in FIG. 1 is data 110 from one or more personal devices ("PD") of one or more subjects. This data 110 may include, for instance, physiological measurements obtained in real time, physiological measurements stored in logs, records of physical activity (e.g., detected using an accelerometer of a mobile device such as a smart phone), logs of dietary information (e.g., food logs maintained by the subjects), and so forth.

In various implementations, an event extractor 112 may be configured to retrieve, from a plurality of data sources such as 102-110, data indicative of a plurality of medical events associated with a subject. As noted, each data source may be different, and may store different data in different ways. For example, some data sources may store structured records in the form of codes, such as codes published by the International Statistical Classification of Diseases and Related Health Problems ("ICD"), which are referred to as "ICD codes." These codes may be adopted by clinicians to classify, for instance, diseases, signs and symptoms, abnormal findings, complaints, social circumstances, and/or external causes of injury or disease. Other data sources may contain data records that are unstructured, such as free-form narratives. For example, clinicians may compose clinical notes when visiting with a subject, and may include a variety of different data in these clinical notes, such as clinician observations and decisions, subject history, demographic data, and so forth. Yet other data sources may include structured fields of raw data, such as demographic data, lab results, physiological measurements, and so forth. Accordingly, event extractor 112 may be configured to extract data indicative of medical events from each data source in different ways.

The terms "medical event" and "medical concept" as used herein refer to individual concepts that relate to specific subjects and also are related to health care and/or to health insurance, and particularly include data points that are useful for patient health prediction. In the health care context they may include, but are not limited to, diagnoses, treatments, observations, lab results, etc. In the health insurance context, medical events may relate to similar concepts as in the medical field, and may also related to insurance-specific concepts such as covered claims, rejected claims, coverage amounts, preexisting conditions, risk assessments, etc. Medical events and medical concepts may also include other data points that are often usable to predict patient health, such as social determinant of health ("SDOH") data, which can include income, income distribution, education, unemployment and job security, food insecurity, housing, etc. In many cases SDOH may be obtained based on all or a portion of a subject's address (e.g., a ZIP code).

Each medical event may be associated with a timestamp that is generated, for instance, at the time the record indicative of the medical event is created, or that may be generated contemporaneously with the medical event itself (e.g., a doctor may make a diagnosis of a particular condition at 3:30 PM on a particular date, a treatment may be applied at 2:45 on a particular date, etc.). The term "timestamp" as used herein refers to an indication of a moment in time. Timestamps can exhibit various levels of granularity, such as down to the second, minute, hour, day, week, month, year, etc. Of particular relevance for the present disclosure are the temporal relationships between medical events/concepts that are signified/determined by timestamps.

As noted above, event extractor 112 may be configured to extract data indicative of medical events from each data source in different ways. As an example, event extractor 112 may utilize a natural language processing ("NLP") module 114 and other similar techniques on a narrative data record that describes, in free form prose, a particular medical event associated with a subject. In some embodiments, NLP module 114 may utilize (e.g., work in conjunction with) a named entity recognizer ("NER") 116 that is configured to recognize clinical terminology defined using standards such as SNOMED. Extracting medical events from structured data records may be more straight-forward, as many fields may be defined in accordance with well-known standards and/or may be clearly labeled with semantic meaning.

In various embodiments, event extractor 112 may construct a medical event by pairing each structured concept with a timestamp of when it was created, and/or by pairing each narrative concept with the creation timestamp of the document from which it was extracted. Patient demographic information may also be used, e.g., by event extractor 112 or other components, to create events. Relevant demographic information may include but is not limited to smoking history, or discrete fields like age/family history, etc., and can in some cases include other types of SDOH. In some embodiments, event extractor 112 may include a data normalizer 118. Data normalizer 118 may be configured to normalize data extracted from different data sources, e.g., so that the normalized data is more amenable to comparison. For example, temperatures may be normalized to Fahrenheit or Celsius, measurements (e.g., physiological measurements, dosages, weight, height, etc.) may be converted to/from the metric system, different medical terms with the same semantic meaning may be aligned (e.g., annotated as being synonymous), etc.

A timeline builder 120 may be configured to receive medical events and timestamps extracted (and normalized where applicable) by event extractor 112 and assemble (and store in a database 121, for instance), what will be referred to herein as a "timeline data structure" that represents a plurality of medical events associated with a subject and a temporal relationship between the plurality of medical events. For example, in some embodiments, a timeline data structure may be represented as a linked list or similar data structure such as a graph. Each node of such a structure may represent a medical event, and may or may not also include the associated timestamp. In some embodiments, edges between nodes may be used to represent a temporal relationships. For example, a weight assigned to an edge between two nodes may represent a time interval between the two medical events corresponding to the two nodes. Additionally or alternatively, other data structures may be used to store timeline data structures, such as related database fields, etc.

In some embodiments, each medical event in a timeline data structure may include data indicative of a link (e.g., a hyperlink) to the original data source from which it was extracted. As will be described shortly, these data may be used by users such as clinicians to view the data and/or context underlying medical events. In some such embodiments, this link data may provide the user with direct access to the original system from which the data was extracted.

A subject history comparer 122 may be configured to compare two or more timeline data structures assembled by timeline builder 120 (and retrieved from database 121) and return results of the comparison. These results may include, for instance, matching medical events (or segments of multiple medical events) and/or a similarity score. The comparison between medical events may be performed, e.g., by subject history comparer 122, based in the content of the medical events (e.g., attributes) and the temporal relationship between the medical events. In various embodiments, the similarity score between individual medical events and/ or between timeline data structures as a whole (i.e., subject similarity) may be determined using various techniques, such as cosine similarity and/or various machine learning techniques. In various embodiments, a user may tune the matching by assigning different priorities and/or weights for criteria such as cosine similarity. In some implementations, the user may also include various constraints, such as exclusion criteria, in the search.

As an example, in some embodiments, to compare two or more medical events or concepts associated with two or more subjects, data from each medical event may be extracted and used to generate a feature vector. The feature vectors of the multiple events may each be embedded into a reduced dimensionality space. A distance between each pair of embeddings may then be determined, e.g., using Euclidian distance, cosine similarity, dot product, etc. The closer two embeddings are, the more similar their corresponding medical events/concepts. Likewise, the farther away the embeddings, the less similar the medical events/concepts.

Additionally or alternatively, in some embodiments, a machine learning model (e.g., neural network) that is used to embed feature vectors may be trained (e.g., as an autoencoder) with at least some semantically labeled training examples of medical event feature vectors. This may, in effect, assign semantic labels to various spaces or clusters of embeddings in the reduced dimensionality space. Thereafter, when an unlabeled medical event feature vector is embedded into the reduced dimensionality space, the "closest" semantic label may be applicable to that medical event. This may be beneficial for identifying similarities between medical events/concepts that are described using different terms or phrases. Additionally or alternatively, in some embodiments, whole timeline data structures, each including multiple medical events/concepts, may be embedded into a reduced dimensionality space, so that similar timeline data structures cluster together in the reduced dimensionality space.

Query user interface ("UI") 124 may be engaged by one or more client devices 126 operated by one or more users that wish to use techniques herein to compare subjects. In various embodiments, query UI 124 may be configured to enable a subject's history (i.e., their timeline data structure) to be rendered on a display as a visual timeline. In various embodiments, a subject's visual timeline may be rendered alongside other visual timelines associated with highly similar subjects (e.g., cohorts) identified by subject history comparer 122. Query UI 124 may also provide the user with the ability to tweak various aspects of the matching behavior, such as tuning similarity parameters, etc.

Client device(s) 126 may include, for example, one or more of: a desktop computing device, a laptop computing device, a tablet computing device, a mobile phone computing device, a computing device of a vehicle of the user (e.g., an in-vehicle communications system, an in-vehicle entertainment system, an in-vehicle navigation system), a stand-alone interactive speaker, a smart appliance such as a smart television, and/or a wearable apparatus of the user that includes a computing device (e.g., a watch of the user having a computing device, glasses of the user having a computing device, a virtual or augmented reality computing device). Additional and/or alternative client computing devices may be provided.

Figure 2:
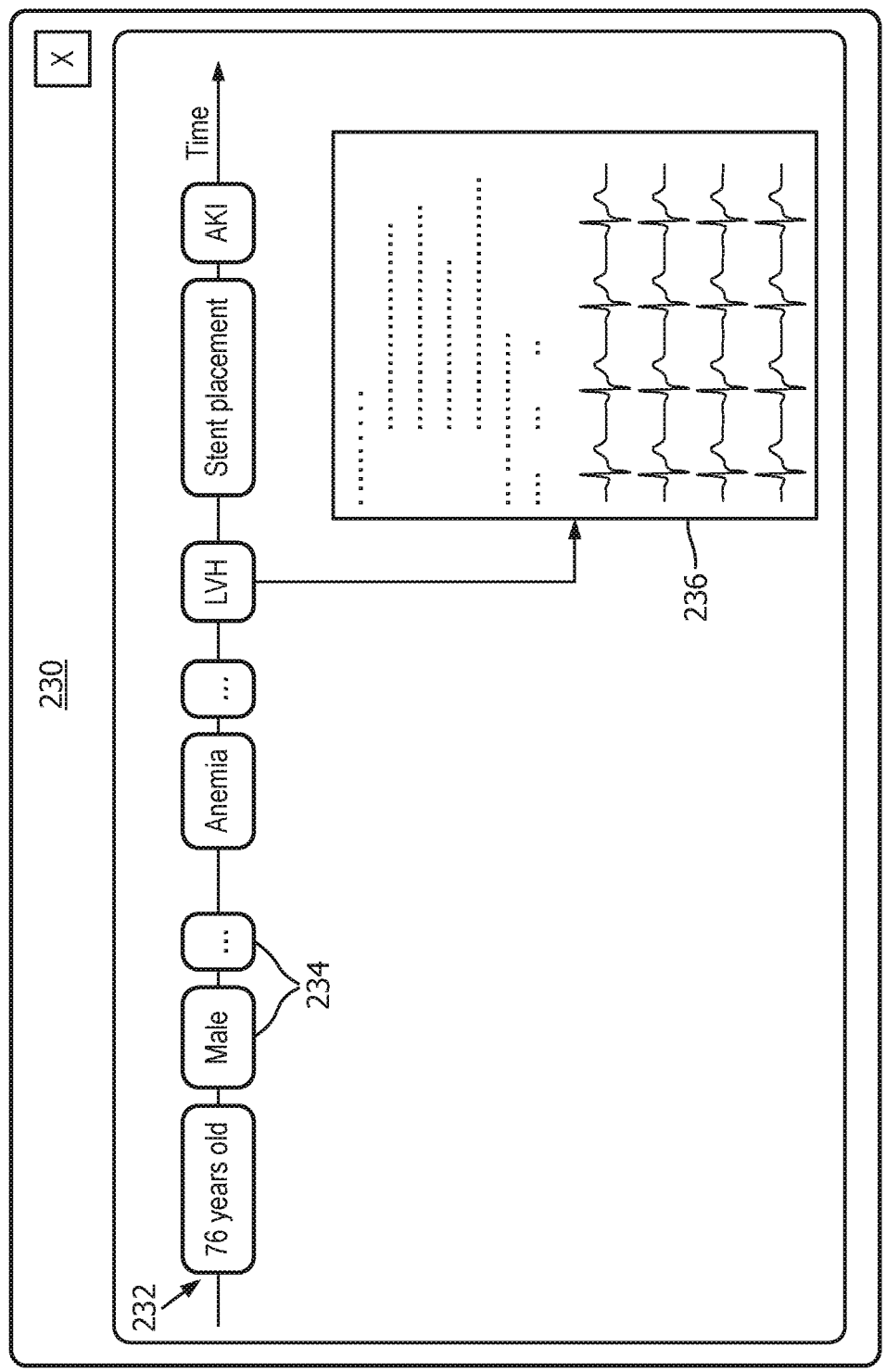
FIG. 2 depicts one example graphical user interface ("GUI") that may be rendered and interacted with, in accordance with various embodiments of the present disclosure.

FIG. 2 depicts an example GUI 230 that may be interacted with by a user to view a visual timeline 232 rendered based on a timeline data structure associated with a subject. In this example, visual timeline 232 includes a plurality of graphical elements 234 (only two which are indicated for the sakes of simplicity and brevity) that are ordered along a time axis from left to right. In this example, the first graphical elements on the left represent various demographic information about the subject, such as his age (76), gender (male), etc. While demographic graphical elements are depicted at the beginning (left side) of visual timeline 232, this is not meant to be limiting. Rather, and for convenience, they are included on the left because they don't necessarily have associated timestamps.

Going from left to right, it can be seen that the subject experienced various medical events, such as an anemia diagnosis, followed sometime later by a diagnosis of left ventricular hypertrophy ("LVH"). This diagnoses lead to a subsequent treatment being applied the form of a stent placement (e.g., percutaneous coronary intervention, or "PCI"). Following the stent placement, the subject was diagnosed with acute kidney injury ("AKI"). As noted previously, in some embodiments, a user may select a graphical element 234, e.g., by clicking on it, double clicking on it, right-clicking on it, etc., to cause an additional interface 236 to be rendered. In FIG. 2 additional interface 236 is rendered as part of the same GUI 230, but this is not meant to be limiting. In this example, the user has selected the graphical element 234 associated with the LVH diagnosis. Consequently, additional interface 236 displays information underlying that diagnosis, such as the depicted ECG readings and/or other data (e.g., features of the ECG readings). In this manner, the user may be able to select a graphical element 234 to view the data underlying the respective medical event.

Figure 3:
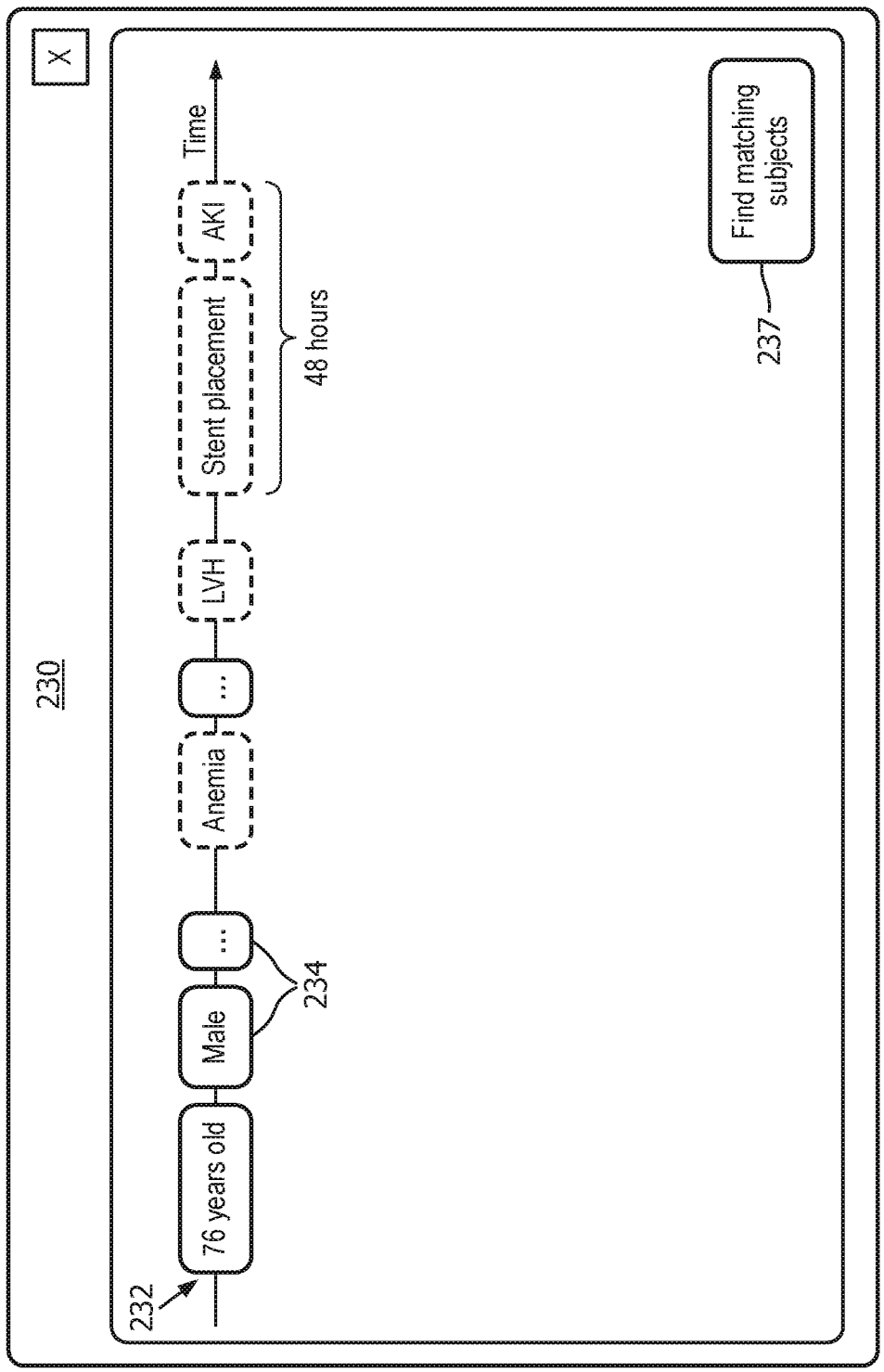
FIG. 3 depicts another example GUI that may be rendered and interacted with, in accordance with various embodiments of the present disclosure.

FIG. 3 depicts an example of how the GUI 230 may be operated by the user to search for similar subjects. In FIG. 3, and as is indicated by the dashed lines, four of the graphical elements 234 have been selected by the user: ANEMIA, LVH, STENT PLACEMENT, and AKI. In effect the user is signaling a desire to see other subjects having experienced a similar sequence of medical events. For example, a cardiologist may wish to view anemic subjects diagnosed with LVH, and that exhibited AKI after a PCI procedure to place a stent in one of the subject's coronary arteries. Based on the user's input selecting these four graphical elements 234, a search query may be formulated, e.g., by subject history comparer 122, that seeks other subjects that experienced an ordered sequence of ANEMIA, LVH, STENT PLACEMENT, and AKI. As indicated by the annotation (which may or may not actually be rendered as part of GUI 230), the STENT PLACEMENT and AKI medical events occurred within 48 hours of one another. This may in fact represent a constraint imposed by the user in the search query to limit or rank responsive results. And for purposes of this ongoing example, it may be assumed that the user imposed an additional constraint that excludes or demotes subjects with diabetes.

Suppose the user now presses the "FIND MATCHING SUBJECTS" button 237 at bottom right. This may cause the search query—formulated based on the user's input selecting the four medical events—to be submitted for searching, e.g., to subject history comparer 122. Responsive data obtained by subject history comparer 122 from database 121 may include timeline data structures associated with other subjects who also experienced the same four medical events in the same general temporal order.

Figure 4:
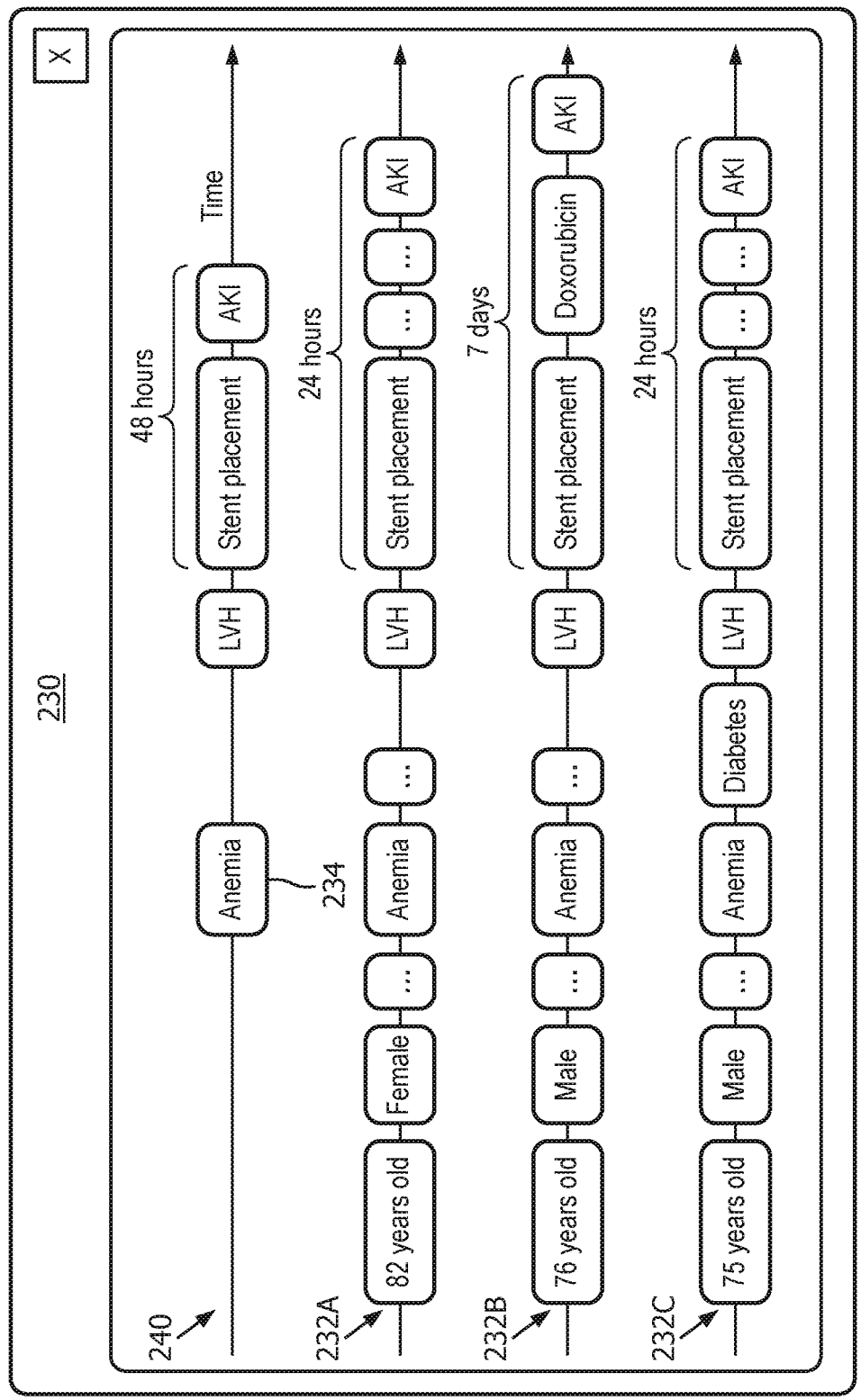
FIG. 4 depicts yet another example GUI that may be rendered and interacted with, in accordance with various embodiments of the present disclosure.

FIG. 4 depicts GUI 230 in a state that may occur after the "FIND MATCHING SUBJECTS" 237 button depicted in FIG. 3 is pressed. In this example, a search query visual timeline 240 is depicted that illustrates the four medical events selected by the user, in their temporal order. Three additional visual timelines 232A-C, are rendered as well. They are associated with three other subjects who experienced the same four medical events in the same order. In this example, visual timeline 232A represents an 82-year-old female subject that had a stent placed, and then was diagnosed with AKI, within twenty four hours. Visual timeline 232B represents a 76-year-old male subject that had a stent placed, and then was diagnosed with AKI, within seven days. Notably, this subject was also treated with doxorubicin (chemotherapy medication) between placement of the stent and the AKI diagnosis. The third visual timeline 232C represents a 75-year-old male subject that had a stent placed, and then was diagnosed with AKI, within twenty four hours. Notably, the third subject was diagnosed with diabetes prior to (or perhaps contemporaneously with) his LVH diagnosis and stent placement.

In this scenario, the first subject, associated with visual timeline 232A, is ranked higher than (e.g., is more similar the original subject) than the others because they were diagnosed with AKI within a day (24 hours) after stent placement. The second subject associated with visual timeline 232B may be ranked lower because seven days passed between his PCI and AKI diagnosis. While the third subject associated with visual timeline 232C was diagnosed in a similar timeframe as the first subject, the third subject was also diagnosed with diabetes, which the user specifically excluded, and so the third subject may be either excluded from the results or at least ranked lower than the others.

Figure 5:
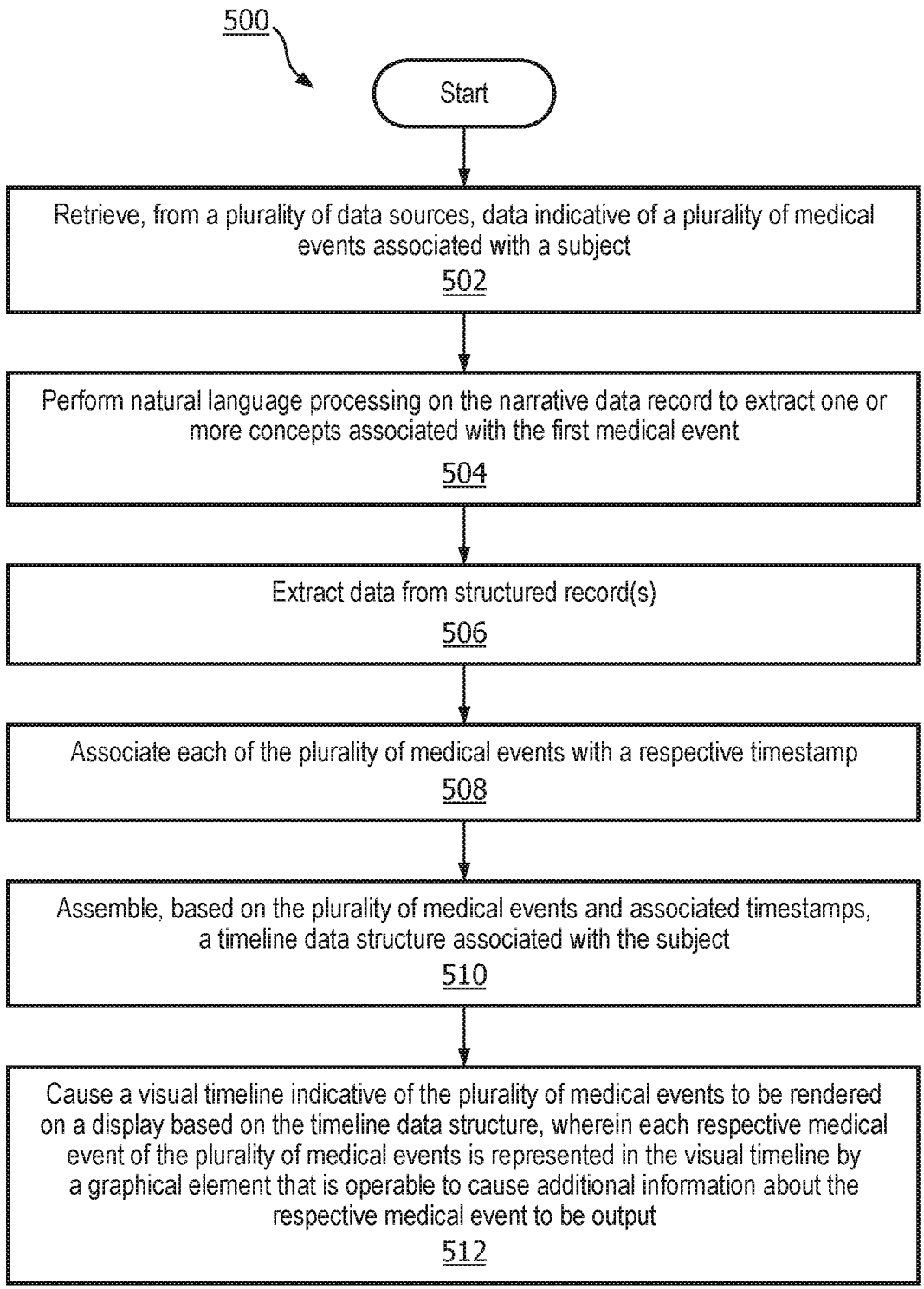
FIG. 5 depicts an example method of performing selected aspects of the present disclosure, in accordance with various embodiments.

FIG. 5 depicts an example method 500 for practicing selected aspects of the present disclosure, in accordance with various embodiments. For convenience, the operations of the flow chart are described with reference to a system that performs the operations. This system may include various components of various computer systems, including those depicted in FIG. 1. Moreover, while operations of method 500 are shown in a particular order, this is not meant to be limiting. One or more operations may be reordered, omitted or added.

At block 502, the system may retrieve, from a plurality of data sources (e.g., 102-110), data indicative of a plurality of medical events associated with a subject. The data may include, for instance, a narrative data record (e.g., a clinical note composed by a clinician) that describes a first medical event of the plurality of medical events associated with the subject, and a structured, non-narrative data record (e.g., an ICD code, physiological measurement, dosages, etc.) that conveys a second medical event of the plurality of medical events associated with the subject. At block 504, the system may perform natural language processing on the narrative data record to extract one or more concepts associated with the first medical event, e.g., so that the first medical event can be assembled from the extracted concepts. At block 506, the system may extract, from the structured, non-narrative data record, one or more additional medical events.

At block 508, the system may associate, e.g., in database 121, each of the plurality of medical events with a respective timestamp. As noted previously, these timestamps may be derived from metadata associated with the underlying data record, or may be explicitly stated in the data record. At block 510, the system may assemble, based on the plurality of medical events and associated timestamps, a timeline data structure associated with the subject. This may be stored in database 121 in some embodiments.

At block 512, the system may cause a visual timeline indicative of the plurality of medical events to be rendered on a display based on the timeline data structure. In various embodiments, the display may be part of a client device (e.g., 126 in FIG. 1) operated by the user, who may be a clinician, researcher, insurance adjuster, etc. In some embodiments, each respective medical event of the plurality of medical events may be represented in the visual timeline by a graphical element (e.g., 234) that is operable to cause additional information (e.g., 236) about the respective medical event to be output.

Figure 6:
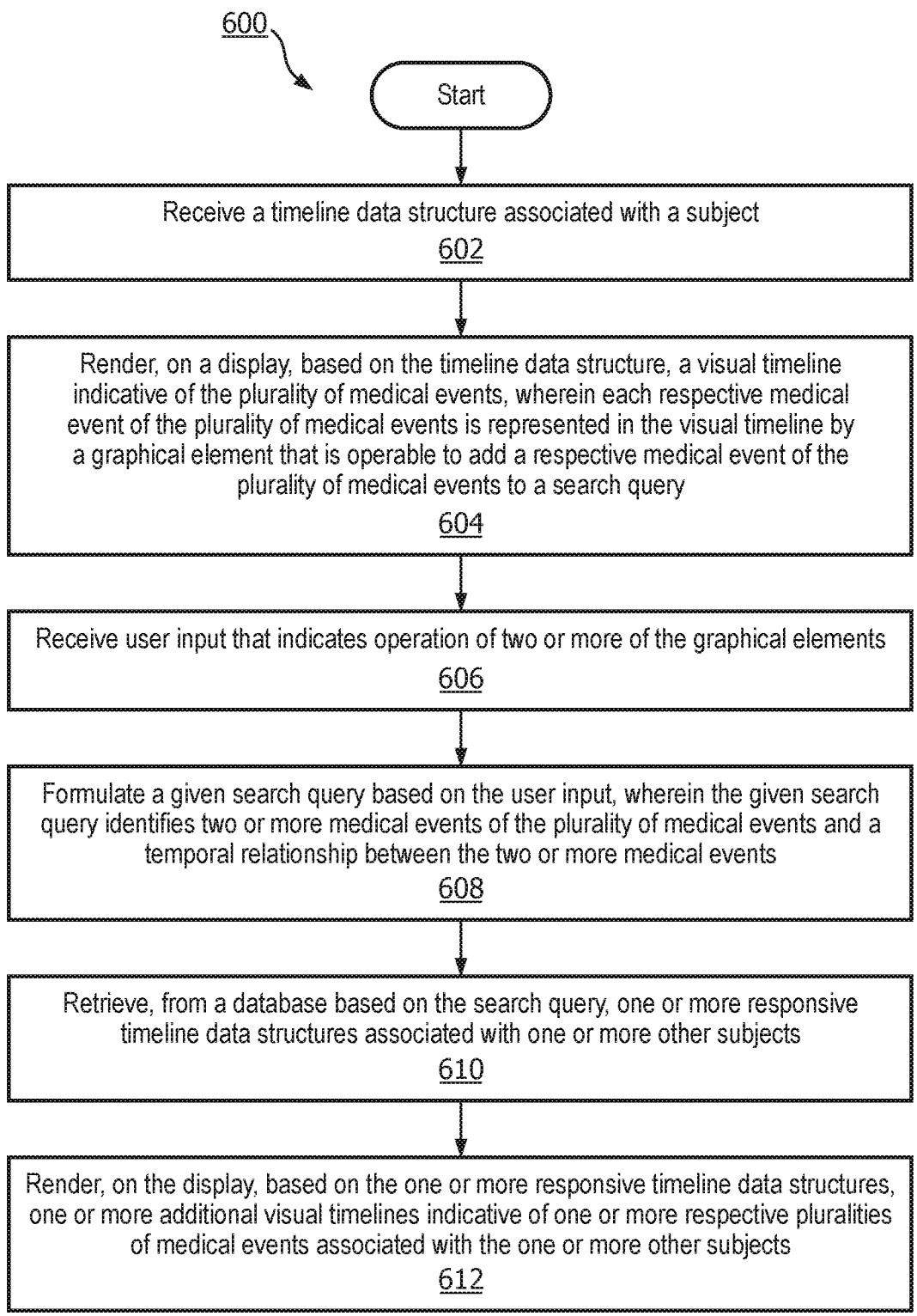
FIG. 6 depicts another example method of performing selected aspects of the present disclosure, in accordance with various embodiments.

FIG. 6 depicts another example method 600 for practicing selected aspects of the present disclosure, in accordance with various embodiments. Method 600 bears some similarities to method 500 but includes slightly different operations. In some embodiments, method 600 may be performed in whole or in part by client device 126, whereas method 500 may be performed at client device 126 and/or at one or more servers, e.g., that implement the components of FIG. 1. For convenience, the operations of the flow chart are described with reference to a system that performs the operations. Moreover, while operations of method 600 are shown in a particular order, this is not meant to be limiting. One or more operations may be reordered, omitted or added.

At block 602, the system may receive a timeline data structure associated with a subject. At block 604, the system may render, on a display, based on the timeline data structure, a visual timeline indicative of the plurality of medical events. In some embodiments, each respective medical event of the plurality of medical events may be represented in the visual timeline by a graphical element that is operable to add a respective medical event of the plurality of medical events to a search query, as depicted in FIG. 3.

At block 606, the system may receive user input that indicates operation of two or more of the graphical elements, e.g., clicking, double-clicking, pressing on a touch screen, dragging, etc. At block 608, the system may formulate a given search query based on the user input. The given search query may identify two or more medical events of the plurality of medical events and a temporal relationship between the two or more medical events.

At block 610, the system may retrieve, from a database (e.g., 121) based on the search query, one or more responsive timeline data structures associated with one or more other subjects. At block 612, the system may render, on the display, based on the one or more responsive timeline data structures, one or more visual timelines indicative of one or more respective pluralities of medical events associated with the one or more other subjects.

As noted previously, techniques described herein may have a wide variety of applications. For example, techniques described herein may be used to identify a cohort of patients that are similar to a patient being examined. Once the cohort is identified, attributes of the cohort (e.g., medical events, treatments, etc.) may be used for clinical decision support and/or to fill in possible missing data items of the patient being examined. As another example, suppose a particular patient is involved with a clinical trial. Techniques described herein may be used to identify other similar patients, who by virtue of this similarity may be reasonably likely to be eligible to participate in the clinical trial.

Additionally or alternatively, techniques described herein may be used to make decisions during insurance claim investigations. For example, suppose a claims adjuster needs to determine whether a given claimant is covered in a particular medical situation. In various embodiments, the insurance adjuster may view a visual timeline associated with the claimant, which may provide a view of the claimant's medical history. The insurance adjuster can then use interactive GUIs provided using techniques described herein to identify similar past claimants. Visual timelines rendered for the other claimants may include information about whether claims were covered, how much of the claims were covered, etc. In this way the insurance adjuster (and more generally, an insurance company) can make sure that insurance claims are covered relatively uniformly across all claims. Additionally or alternatively, techniques and systems described herein may be used to assess risks associated with new customers, e.g., to determine deductibles, premiums, etc.

Figure 7:
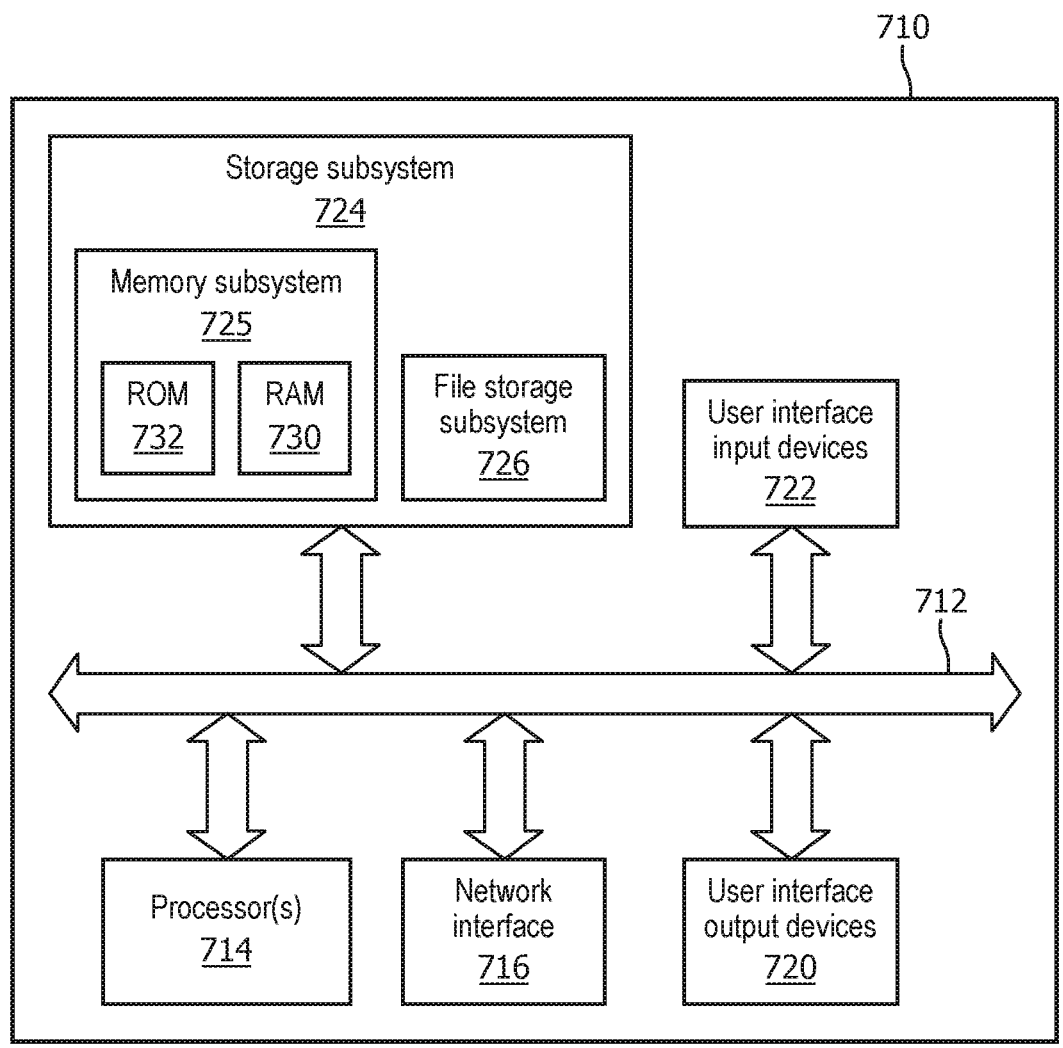
FIG. 7 depicts an example computing system architecture.

FIG. 7 is a block diagram of an example computing device 710 that may optionally be utilized to perform one or more aspects of techniques described herein. In some implementations, one or more of a client computing device, user-controlled resources engine 130, and/or other component(s) may comprise one or more components of the example computing device 710.

Computing device 710 typically includes at least one processor 714 which communicates with a number of peripheral devices via bus subsystem 712. These peripheral devices may include a storage subsystem 724, including, for example, a memory subsystem 725 and a file storage subsystem 726, user interface output devices 720, user interface input devices 722, and a network interface subsystem 716. The input and output devices allow user interaction with computing device 710. Network interface subsystem 716 provides an interface to outside networks and is coupled to corresponding interface devices in other computing devices.

User interface input devices 722 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 710 or onto a communication network.

User interface output devices 720 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 710 to the user or to another machine or computing device.

Storage subsystem 724 stores programming and data constructs that provide the functionality of some or all of the modules described herein. For example, the storage subsystem 724 may include the logic to perform selected aspects of the methods of FIGS. 5-6 and 11, as well as to implement various components depicted in FIGS. 1 and 8.

These software modules are generally executed by processor 714 alone or in combination with other processors. Memory 725 used in the storage subsystem 724 can include a number of memories including a main random access memory (RAM) 730 for storage of instructions and data during program execution and a read only memory (ROM) 732 in which fixed instructions are stored. A file storage subsystem 726 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 726 in the storage subsystem 724, or in other machines accessible by the processor(s) 714.

Bus subsystem 712 provides a mechanism for letting the various components and subsystems of computing device 710 communicate with each other as intended. Although bus subsystem 712 is shown schematically as a single bus, alternative implementations of the bus subsystem may use multiple busses.

Computing device 710 can be of varying types including a workstation, server, computing cluster, blade server, server farm, or any other data processing system or computing device. Due to the ever-changing nature of computers and networks, the description of computing device 710 depicted in FIG. 7 is intended only as a specific example for purposes of illustrating some implementations. Many other configurations of computing device 710 are possible having more or fewer components than the computing device depicted in FIG. 7.

In addition to finding similar subjects, in another aspect, techniques described herein may be used to identify inconsistencies or conflicts between medical events/concepts associated with a particular subject. These inconsistencies may then be presented, e.g., using a visual timeline interface similar to those depicted in FIGS. 2-4. The presented inconsistencies may be useful for a variety of purposes. As one example, the inconsistencies identified among a plurality of subjects, e.g., patients of a particular healthcare provider, can be used to identify institutional problems and/or inefficiencies, so that they can be addressed at a policy level. As another example, an insurance adjuster could use these tools to determine whether to pay a claim. For example, if a medical bill submitted for reimbursement is for a treatment that is inconsistent with the submitter's medical history (determined using techniques described herein), the insurance adjuster might elect not to pay the claim, or at least to investigate further.

Figure 8:
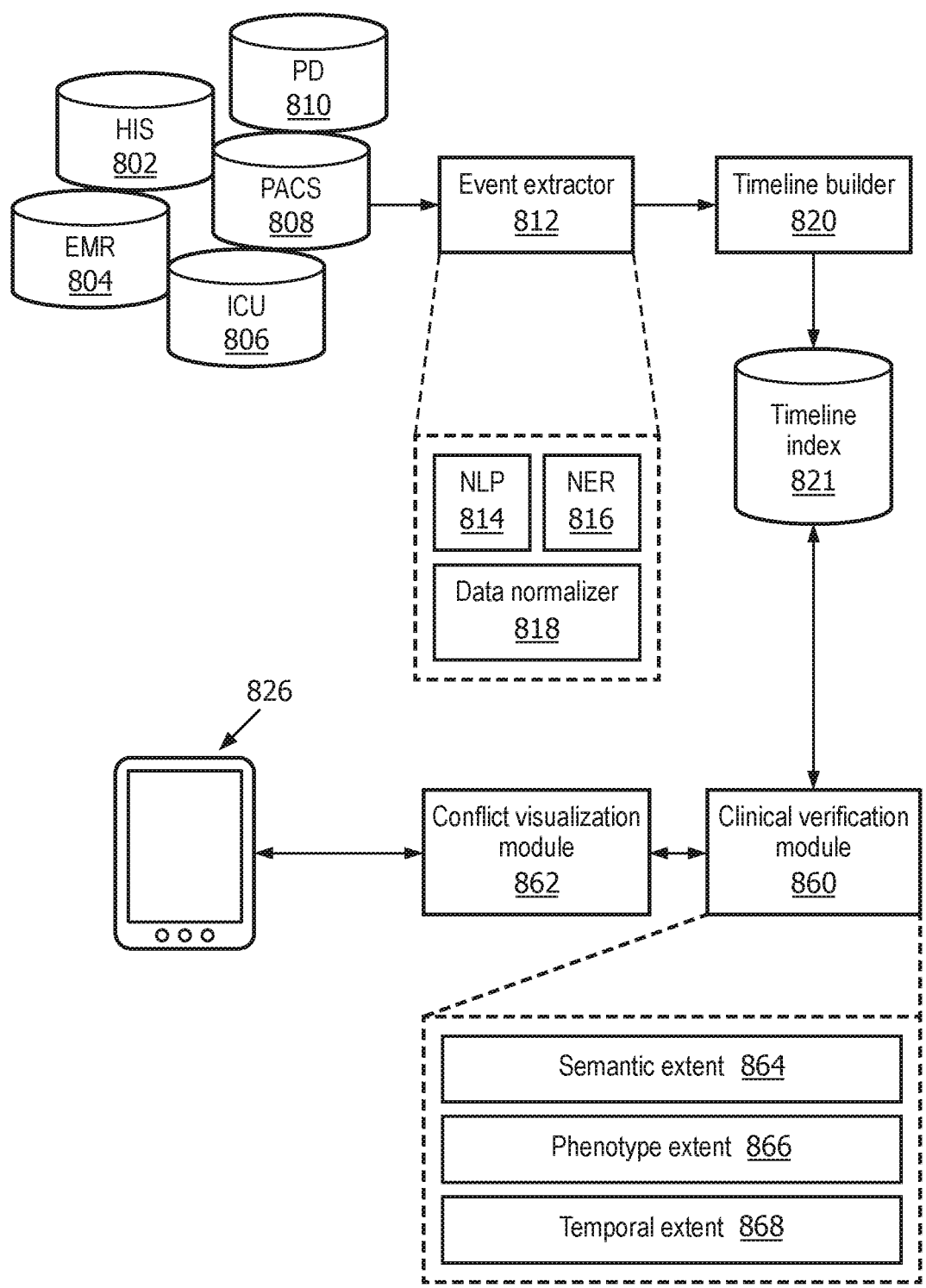
FIG. 8 illustrates another example environment in which selected aspects of the present disclosure may be implemented, in accordance with various embodiments.

FIG. 8 depicts an example environment that is very similar to that depicted in FIG. 1. In fact, components 802-821 may be similar to, or even identical to, components 102-121 depicted in FIG. 1, and therefore will not be described again in detail. As was the case with FIG. 1, the various components depicted in FIG. 8 may be implemented using any combination of software and hardware. In some embodiments, one or more components may be combined, e.g., as part of a "cloud" computing system that is available to clinicians, insurance personnel, etc.

A clinical verification module 860 may be configured to identify, based on timeline data structure(s) stored in database 821 (e.g., similar to database 121), inconsistencies in a particular subject's timeline. Inconsistencies may take various forms. For example, a first diagnosis of diabetes might not be compatible with a second diagnosis of hypoglycemia, especially if the two diagnoses occur within a relatively short amount of time. More examples of inconsistencies between medical events will be described below.

In various embodiments, clinical verification module 860 may include one or more of a semantic extent 864, a phenotype extent 866, and a temporal extent 868. These extents may include rules, models (e.g., trained machine learning models), constraints, decision trees, guidelines, heuristics, and anything other decision-making mechanism that might help clinical verification module 860 determine whether an inconsistency/conflict exists for a particular subject.

In various embodiments, semantic extent 864 may include one or more rules or guidelines that are usable, e.g., by clinical verification module 860, to quantify consistency between medical events (or concepts) on a given subject's timeline. As an example, there may be a defined measure for the extent of a given medical event/concept A, so that it is possible to determine whether another medical event/concept B has the same or different semantic meaning. In some implementations, semantic extent 864 may employ identity relationships, such as "IsA" in SNOMED-CT, that already exist in medical ontologies to define the extent of a particular medical event/concept. Under this paradigm, medical event/concept A and medical event/concept B may be deemed to be consistent with each other if and only if medical event/concept A is a direct line ancestor of medical event/concept B (via the identity relationship), or vice a versa. Using such an extent it is possible to ensure that "lung cancer" is consistent with "cancer" but not consistent with "liver cancer."

Phenotype extent 866 may include one or more rules or guidelines that are usable, e.g., by clinical verification module 860, to determine whether two or more medical events/concepts are consistent with each other from a rules-based phenotype approach. The term "phenotype" is used herein to describe a high-level clinical entity that is derived from a combination of two or more basic (or granular) clinical concepts, or even from other phenotypes. Phenotype may be defined, for example, by clinical organizations such as American College of Cardiology ("ACC"), or the Radiology Society of North America ("RSNA"). As an example, the Society of Thoracic Surgeons, in their "Acute Coronary Syndromes Data Standard" (JACC 2001 38:2114-30) paper, published a definition for "Hypertension." The National Cardiovascular Data Register ("NCDR") also has its own definition.

In some embodiments, a rules-based approach may be employed as part of phenotype extent 866. For example, in some embodiments, a decision tree for a particular medical event/concept may be designed based on a corresponding phenotype. For each episode of care, the rule-based and/or decision tree-based reasoning may be executed using subject data. A conflict or inconsistency may be detected, for instance, where output generated by traversal of a decision tree indicates a contradictory result within the same episode of care and/or across different episodes of care within a valid time interval.

Figure 9:
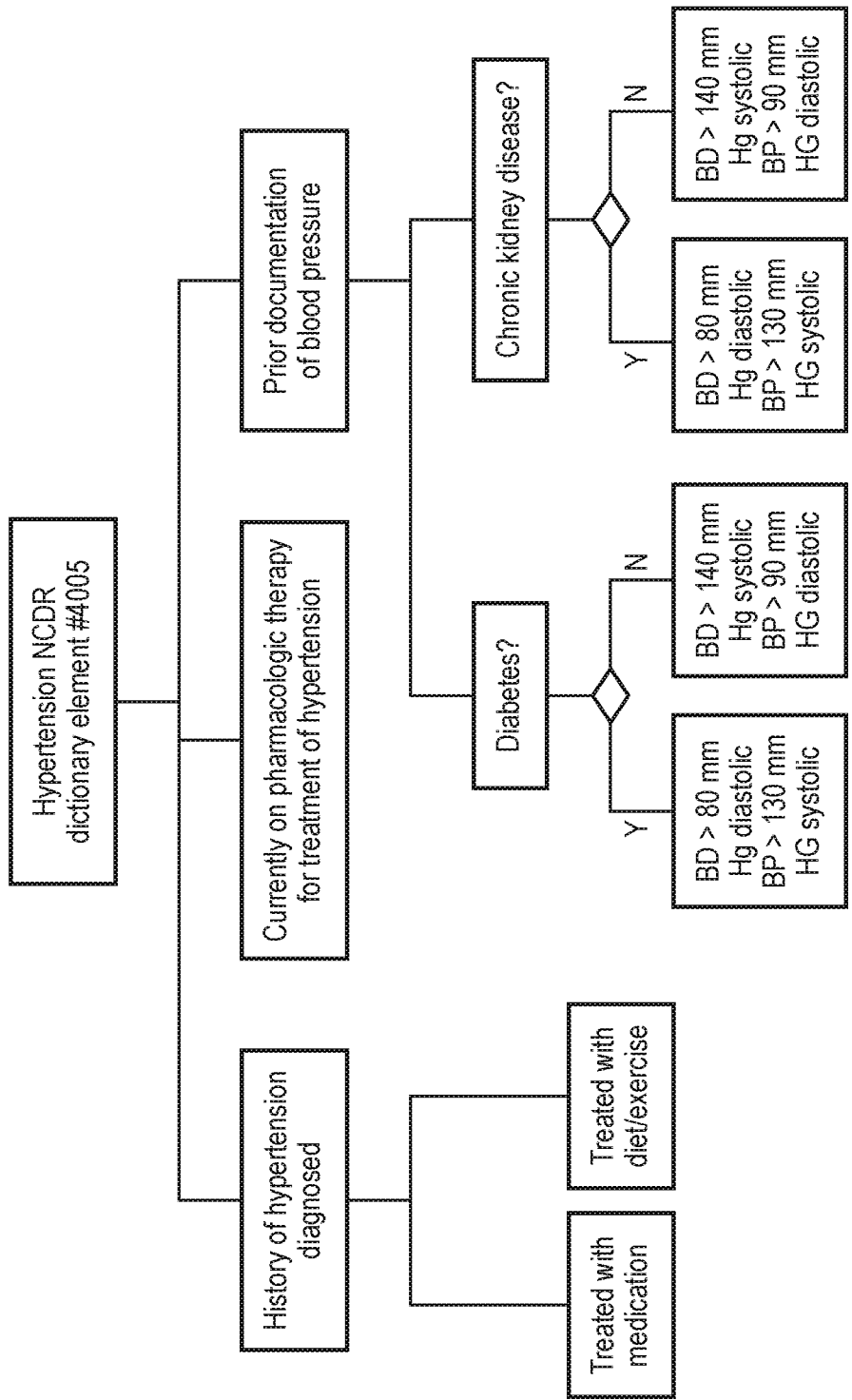
FIG. 9 depicts an example of a decision-tree that may be employed to identify inconsistencies/conflicts between medical events/concepts associated with a subject.

FIG. 9 depicts one example decision tree that may be employed for diagnosing the medical event/concept of hypertension. A root node represents the high level concept. Three first-level child nodes represent three different scenarios in which hypertension can be diagnosed: a history of diagnosed hypertension; currently on pharmacologic therapy for treatment of hypertension; or prior documentation of blood pressure that suggests hypertension. As is shown in FIG. 9, for the third child-node of the root node ("PRIOR DOCUMENTATION OF BLOOD PRESSURE"), there are two children trees that are applicable if the subject has diabetes or chronic kidney disease, respectively. The logic represented by the decision tree of FIG. 9 may be applied, for instance, to verify whether a particular subject's diagnosis of hypertension by a clinician is consistent with the subject's larger medical history.

In addition to or instead of a rules-based or decision tree-based approach, in some embodiments, phenotype extent 866 may employ one or more trained machine learning models to identify inconsistencies or conflicts across medical events associated with subjects. As a non-limiting example, a typical episode of care that commonly leads to a particular diagnosis may involve a particular lab with a particular set of results and/or other observations. In some embodiments, supervised learning may be used to train a machine learning model such as a support vector machine, neural network, Bayesian classifier, etc., to classify a subject has having or not having the diagnosis based on these lab results and/or other observations. Training data may include a plurality of training examples, each including a feature vector that represents the lab results/observations of a particular patient. Each training example may be labeled with the respective patient's diagnosis, and may be applied as input across the machine learning model to generate output. The output may be compared with the label, and based on a difference (or "loss") between the label and the output, various training techniques, such as gradient descent and/or back propagation, may be employed to train the model. Once trained, such a model may be used to verify a diagnosis of a subject (or detect a conflict), e.g., based on various data points associated with the same episode of care as the diagnosis and/or across multiple episodes of care.

Figure 10:
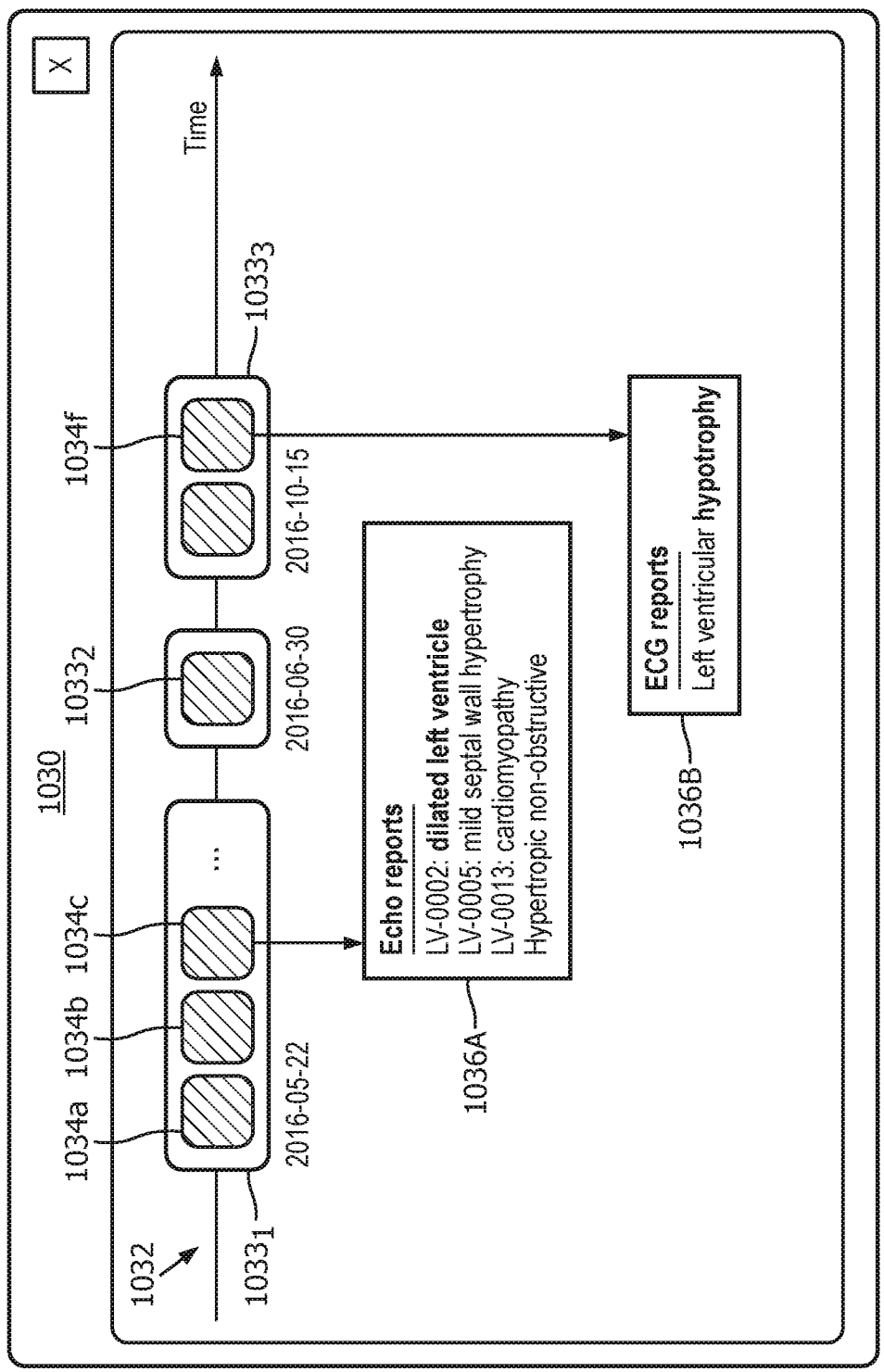
FIG. 10 depicts an example graphical user interface, in accordance with various embodiments.

As an example, FIG. 10 depicts a GUI 1030 that is similar to GUIs of previous Figures. Once again a visual timeline 1032 associated with a subject is displayed. In this example, visual timeline 1032 is organized by episodes of care 1033$_1$-$_3$. Each episode of care may represent, for instance, a visit or appointment with a clinician, and one or more graphical elements 1034 associated with one or more medical events/concepts 1034 may be associated with each episode of care 1033. Thus, first episode of care 1033$_1$ occurred on 2016 May 22, and included three medical events/concepts represented by graphical elements 1134$a$-$c$. Second episode of care 1033$_2$ occurred on 2016 Jun. 30, and included one medical event/concept represented by graphical element 1134$d$. And so on.

Suppose that during first episode of care 1033$_1$, the subject undergoes an electrocardiograph ("ECG") that evidences an echocardiogram that evidences, as a medical event represented by graphical element 1034$c$, left ventricular hypotrophy ("LVH"). Now, suppose that later, during a third episode of care 1033$_3$, an echocardiograph ("ECHO") is performed and is the basis for a diagnosis of a dilated left ventricle. LVH is inconsistent with a dilated left ventricle.

In some embodiments, such an inconsistency may be detected by application of a trained machine learning model. For example, in FIG. 10, a LVH is indicated during the first episode of care 10331 (dated 2016 May 22). However, the trained machine learning model may be applied to study other characteristics of the test performed during this episode of care (1033$_1$). For example, if S in V2 and the R wave in V6 are both below a threshold of 35 mm, and R in a VL is smaller than 11 mm, the trained machine learning model may predict this case to be "not LVH." Thus, a conflict is detected.

Referring back to FIG. 8, in addition to or instead of the rules/decision-tree-based approaches and/or machine learning models, phenotype extent 866 may include other mechanisms that are usable by clinical verification module 860 to identified conflicts and/or inconsistencies. For example, in some embodiments, codes provided by various standard clinical ontology coding schemes, such as SNOMED, ICD10, RadLex, etc., may be well-structured. Parent codes may be inclusive of children codes, content-wise. Accordingly, these codes may be used to detect conflicts and/or consistencies. As a non-limiting example, a conflict might be raised if an ICD-10 code of I11.9 (hypertensive heart disease without heart failure) is detected during one episode of care, but hypertensive heart disease is ruled out during the same episode of care or a different (but temporally-proximate) episode of care.

Temporal extent 868 may include one or more time-related constraints, rules, etc., that are used, e.g., by clinical verification module 860, to determine what timeframe medical events/concepts should be considered within. Take, for example, the different medical concepts: "fever", "smoker", and "HIV." All of these have different time frames associated with them, and they should not necessarily be compared for purposes of detecting conflicts. In some embodiments, each of the plurality of medical events associated with a subject may be classified into one of a predetermined number of temporal categories, such as acute, chronic, and/or indeterminate. With these temporal classifications, clinical verification module 860 can limit the scope of consistency checks. In some such embodiments, clinical verification module 860 may refrain from comparing two medical events of the plurality of medical events that are classified into incompatible temporal categories. For example, there is no need to determine whether a fever three years ago (an acute event) is consistent with a currently present condition.

In various embodiments, conflict visualization module 862 may be configured to render, or cause to be rendered, output indicative of inconsistencies and/or conflicts identified by clinical verification module 860. For example, in various embodiments, one or more client devices 826 operated by, for example, clinicians, researchers, insurance adjusters/investigators, etc., may be used to connect to conflict visualization module 862 (e.g., using a web interface) and view data indicative of conflicts/inconsistencies. These conflicts may be output in various ways.

In some embodiments, conflict visualization module 862 may cause an interface similar to that depicted in FIG. 10 to be rendered, e.g., on client device 826. In FIG. 10, the conflict is visually emphasized by the two interfaces 1036A and 1036B, as well as the arrows leading from the graphical elements 1034 associated with the conflicting medical events/concepts to the interfaces 1036A and 1036B. An arrow from graphical element 1034$c$ leads to first interface 1036A, which provides details about the ECHO test performed during the third episode of care 1033$_3$ that yielded the inconsistent (relative to the diagnosis of LVH underlying graphical element 1033$c$) medical event/concept of left ventricle dilation. Similarly, an arrow from graphical element 1034$f$ leads to second interface 1036B, which provides details about the ECG test performed during the first episode of care 1033$_1$ that yielded the inconsistent (relative to the diagnosis of left ventricle dilation underlying graphical element 1034$f$) medical event/concept of LVH. In this manner, the user (e.g., clinician, insurance adjuster, researcher, etc.) is able to quickly identify which medical events/concepts are in conflict, and to view the underlying data to investigate further.

Figure 11:
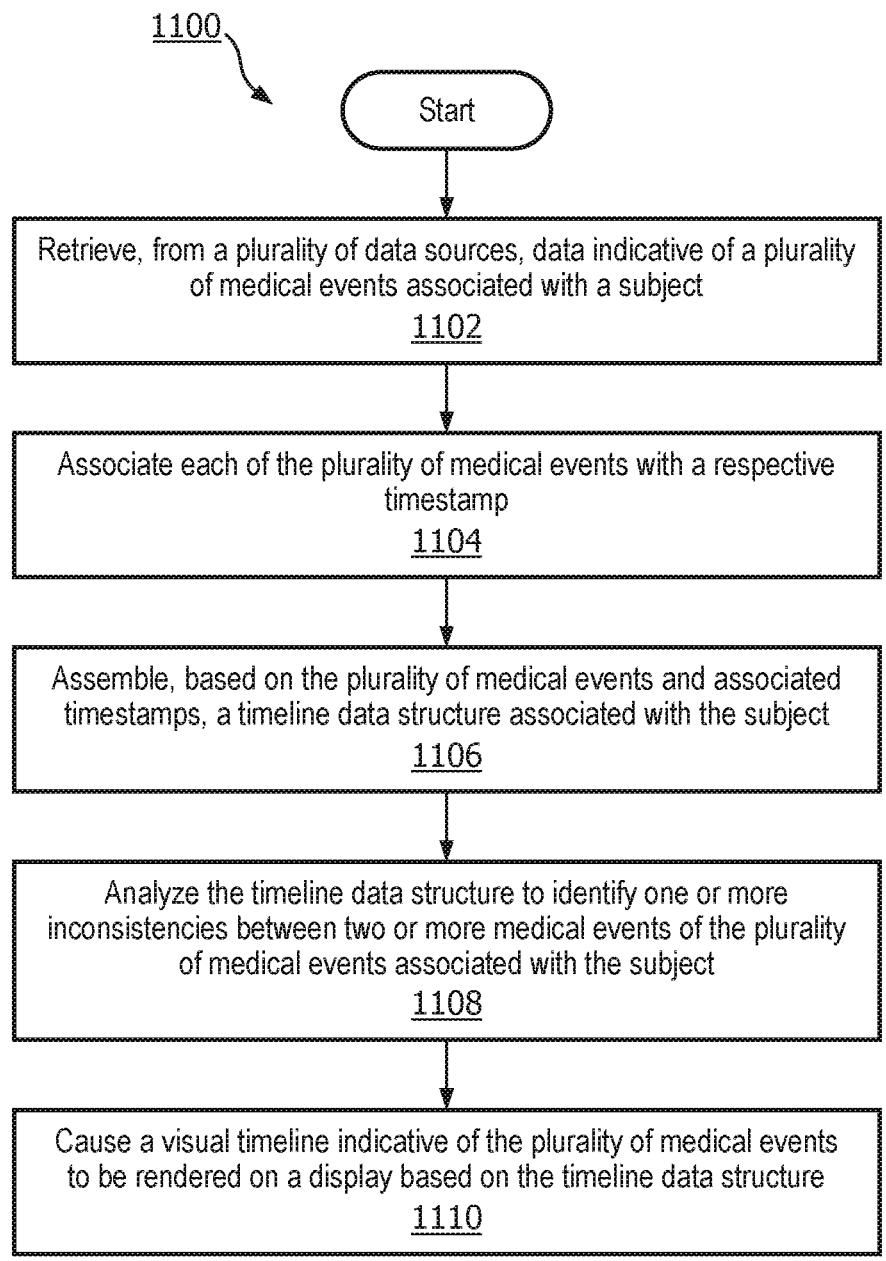
FIG. 11 depicts an example method of performing selected aspects of the present disclosure, in accordance with various embodiments.

FIG. 11 depicts an example method 1100 for performing selected aspects of the present disclosure, including detecting conflicts/inconsistencies in subject timelines. For convenience, the operations of the flow chart are described with reference to a system that performs the operations. This system may include various components of various computer systems, including those depicted in FIGS. 1 and/or 8. While the operations of FIG. 11 are depicted in a particular order, this is not meant to be limiting. In various embodiments, one or more operations may be added, omitted, and/or reordered.

At block 1102, the system may retrieve, e.g., from a plurality of data sources (e.g., 802-810), data indicative of a plurality of medical events associated with a subject, similar to block 502 of FIG. 5. At block 1104, the system may associate each of the plurality of medical events with a respective timestamp, similar to operation 508 of FIG. 5. At block 1106, the system may assemble, based on the plurality of medical events and associated timestamps, a timeline data structure associated with the subject, similar to block 510 of FIG. 5.

At block 1108, the system, e.g., by way of clinical verification module 860, may analyze the timeline data structure to identify one or more inconsistencies (which would include conflicts) between two or more medical events of the plurality of medical events associated with the subject. As described previously, inconsistencies may be identified using a variety of techniques, such as rules-based approaches (e.g., see decision tree in FIG. 9), one or more trained machine learning models, etc. In various embodiments, the comparisons of medical events may be limited/guided by the extents 864-868 depicted in FIG. 8.

At block 1110, the system, e.g., by way of conflict visualization module 862, may cause a visual timeline indicative of the plurality of medical events to be rendered on a display (e.g., of client device 826) based on the timeline data structure. In some embodiments, each respective medical event of the plurality of medical events may be represented in the visual timeline by a graphical element. In some such embodiments, two or more of the graphical elements that are associated with the two or more medical events for which the one or more inconsistencies were identified at block 1108 may be visually distinguished from other graphical elements, e.g., as shown in FIG. 9.

Identifying inconsistencies/conflicts in medical timelines may have a variety of applications. As one example, timelines of multiple subjects may be analyzed to determine, for instance, a level of consistency associated with a particular clinician, a particular department, a particular hospital, or even across an entire health care system. As another example, techniques described herein may be used to identify compliance with particular standards. Conflicts between actual treatment received by a subject and accepted standards might be identified and used, for instance, as evidence in litigation.

As yet another example, techniques described herein may be used to link conflicts (or lack thereof) with reimbursement procedures. Consequently, reimbursement may be applied more consistently across similar cases. As yet another example, techniques described herein may be used with a particular subject's history to drill down and identify potential causes of poor outcomes, and could even be used to generate a priority list of problems associated with the subject, to be addressed in a health care environment.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A timeline generation system for generating a subject timeline, comprising:
   a plurality of data sources, each comprising data indicative of one or more of a plurality of historical medical events associated with a subject;
   a remote user device comprising:
      (i) a user interface configured to display a visual timeline indicative of the plurality of historical medical events associated with the subject and based on a timeline data structure, and further configured to receive a request from a user to display one or more additional visual timelines associated with one or more other subjects and that are similar to the displayed visual timeline, and a selection of a graphical element representing a historical medical event from the displayed visual timeline; and
      (ii) a communication interface configured to receive the visual timeline and to communicate the received request and the selection; and
   a timeline generator remote from the remote user device and comprising:
      (i) a communication interface configured to communicate the visual timeline and to receive the communicated request and communicated selection; and
      (ii) a processor configured to:
         (1) retrieve, from the plurality of data sources, the data indicative of the plurality of historical medical events associated with the subject;
         (2) associate each of the plurality of historical medical events with a respective timestamp;
         (3) assemble, based on the plurality of historical medical events and associated timestamps, the timeline data structure associated with the subject;
         (4) analyze the timeline data structure to identify one or more inconsistencies between two or more historical medical events of the plurality of historical medical events associated with the subject;
         (5) cause the visual timeline indicative of the plurality of historical medical events to be rendered on the display of the remote user device based on the timeline data structure, wherein each respective medical event of the plurality of historical medical events is represented in the displayed visual timeline by a graphical element;
         (6) receive the selection of the graphical element from the remote user device;
         (7) adjust the rendered display to provide additional information associated with the historical medical event represented by the selected graphical element;
         (8) receive the request to display one or more additional visual timelines similar to the displayed visual timeline, wherein the received request includes a further selection of the graphical elements corresponding to at least two historical medical events in the displayed visual timeline, wherein the graphical elements corresponding to the at least two historical medical events are in a temporal order in the displayed visual timeline;
         (9) generate, in response to the received request, an updated visual timeline comprising the displayed visual timeline of the subject aligned with the one or more additional visual timelines, wherein the one or more additional visual timelines are similar to the displayed visual timeline of the subject, and wherein each of the one or more additional visual timelines in the updated visual timeline includes the graphical elements corresponding to the at least two medical events in the temporal order; and
         (10) cause the updated visual timeline to be rendered on the display of the remote user device;
      wherein two or more of the graphical elements that are associated with the two or more historical medical events for which the one or more inconsistencies were identified are visually distinguished from other graphical elements in the displayed visual timeline, wherein one or more of the displayed graphical elements are selectable.

2. The timeline generation system of claim 1, wherein the analyzing comprises semantically analyzing the plurality of medical events, and the one or more inconsistencies include one or more semantic inconsistencies.

3. The timeline generation system of claim 1, wherein the analyzing comprises searching for identity relationships between two or more of the plurality of medical events.

4. The timeline generation system of claim 1, wherein the analyzing comprises applying attributes of at least two of the plurality of historical medical events as input across a trained machine learning model to generate output, wherein the output is indicative of the one or more inconsistencies.

5. The timeline generation system of claim 1, wherein the analyzing includes navigating a phenotype decision tree based on attributes of at least two of the plurality of medical events.

6. The timeline generation system of claim 1, wherein the processor is further configured to classify each of the plurality of historical medical events into one of a predetermined number of temporal categories.

7. The timeline generation system of claim 6, wherein the analyzing includes refraining from comparing two historical medical events of the plurality of historical medical events that are classified into incompatible temporal categories.

8. A method for generating a subject timeline, comprising:
   providing a timeline generation system, comprising a timeline generator comprising one or more processors, and further comprising a remote user device in communication with but remote from the timeline generator;
   retrieving, by the timeline generator from a plurality of data sources, data indicative of a plurality of historical medical events associated with a subject;
   associating each of the plurality of historical medical events with a respective timestamp;
   assembling, by the timeline generator based on the plurality of historical medical events and associated timestamps, a timeline data structure associated with the subject;
   analyzing the timeline data structure to identify one or more inconsistencies between two or more historical medical events of the plurality of historical medical events associated with the subject;

causing, by the timeline generator, a visual timeline indicative of the plurality of historical medical events to be rendered on a display of the remote user device based on the timeline data structure, wherein each respective historical medical event of the plurality of historical medical events is represented in the visual timeline by a graphical element, and wherein two or more of the graphical elements that are associated with the two or more historical medical events for which the one or more inconsistencies were identified are visually distinguished from other graphical elements, wherein one or more of the displayed graphical elements are selectable;

receiving, from a user via the display, a selection of a graphical element representing a historical medical event from the displayed visual timeline;

adjusting, by the timeline generator, the rendered display to provide additional information associated with the historical medical event represented by the selected graphical element; and receiving, from the user via the display of the remote user device, a request to display one or more additional visual timelines for one or more other subjects and that are similar to the displayed visual timeline, wherein the received request includes a further selection of the graphical elements corresponding to at least two historical medical events in the displayed visual timeline, wherein the graphical elements corresponding to the at least two historical medical events are in a temporal order in the displayed visual timeline;

generating, in response to the received request, an updated visual timeline comprising the displayed visual timeline of the subject aligned with the one or more additional visual timelines, wherein the one or more additional visual timelines are similar to the displayed visual timeline of the subject, and wherein each of the one or more additional visual timelines in the updated visual timeline includes the graphical elements corresponding to the at least two medical events in the temporal order; and causing the updated visual timeline to be rendered on the display of the remote user device.

9. The method of claim 8, further comprising the steps of:

determining, by a user of the timeline generation system based on the rendered updated visual timeline, whether to pay an insurance claim for the subject; and implementing the decision whether to pay the insurance claim for the subject.

10. The method of claim 8, further comprising the steps of:

determining, by a user of the timeline generation system based on the rendered updated visual timeline, an insurance deductible or premium for the subject; and implementing the determined insurance deductible or premium for the subject.

11. The method of claim 8, further comprising the steps of: determining, based on at least the identified one or more inconsistencies between two or more historical medical events of the plurality of historical medical events associated with the subject, whether to pay an insurance claim for the subject; and implementing the decision whether to pay the insurance claim for the subject.

* * * * *